US00PP29127P2

(12) United States Plant Patent
Bradford et al.

(10) Patent No.: US PP29,127 P2
(45) Date of Patent: Mar. 20, 2018

(54) NECTARINE TREE NAMED 'RED BRIGHT IT'

(50) Latin Name: *Prunus persica*
Varietal Denomination: Red Bright II

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 15/530,226

(22) Filed: Dec. 15, 2016

(51) Int. Cl.
*A01H 5/08* (2006.01)

(52) U.S. Cl.
USPC ..... Plt./190

(58) Field of Classification Search
USPC ..... Plt./190
See application file for complete search history.

(56) References Cited

U.S. PATENT DOCUMENTS

PP7,507 P 4/1991 Bradford
PP18,715 P2 4/2008 Bradford

*Primary Examiner* — Annette H Para

(57) ABSTRACT

The present invention relates to a new and distinct variety of nectarine tree, *Prunus persica*, broadly characterized by a large size, vigorous, hardy, self-fertile, productive and regular bearing tree. The variety blooms during the mid season and requires about 525 chilling hours. The fruit matures under the ecological conditions described in mid June, with first picking on Jun. 10, 2016. The fruit is large in size, globose to slightly oblong in shape, clingstone in type, firm in texture, yellow with red bleeding in flesh color, full red in skin color, and acidic in flavor.

1 Drawing Sheet

Botanical classification: *Prunus persica.*
Variety denomination: 'Red Bright II'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Red Bright II'.

The present variety was hybridized by us in 2008 as a first generation cross using a '5P452' white flesh nectarine (unpatented) as the selected seed parent and 'Kay Diamond VII' (U.S. Plant Pat. No. 18,715) nectarine, as the selected pollen parent. Upon reaching maturity the fruit of this cross was gathered, and the seeds were removed, cracked, stratified, germinated, and grown as seedlings on their own root in our greenhouse. Upon reaching dormancy the seedlings were transplanted as a group to a cultivated area of our experimental orchard located near Le Grand, Calif., in Merced County (San Joaquin Valley). During the fruit evaluation season of 2012 we selected the present variety as a single tree from the group of seedlings described above. Subsequent to origination of the present variety of nectarine tree, we asexually reproduced it by budding and grafting in the experimental orchard described above, and such reproductions were true to the original tree in all respects. The reproduction of the variety included the use of 'Nemaguard' (unpatented) rootstock upon which the present variety was compatible and true to type.

The present variety is similar to its seed parent, '5P452' (unpatented) nectarine, by producing nectarines that are firm, mostly red in skin color, nearly globose in shape, and clingstone in type, but is quite distinguished therefrom by producing fruit that is yellow instead of white in flesh color and acidic instead of sub-acidic in flavor.

The present variety is similar to its pollen parent, 'Kay Diamond VII' (U.S. Plant Pat. No. 18,715) nectarine, by producing nectarines that are medium to large in size, firm in texture, mostly red in skin color, nearly globose in shape, clingstone in type, acidic in flavor, and yellow in flesh color, but is quite distinguished therefrom by having globose leaf glands instead of being eglandular, by blooming in the mid season instead of early, and by producing fruit that matures about twenty-five days later.

The present variety is most similar to 'Spring Bright' (U.S. Plant Pat. No. 7,507) nectarine by being self-fertile, by blooming in the mid season, by having globose leaf glands, and by producing nectarines that are firm in texture, mostly red in skin color, yellow in flesh color, nearly globose in shape, clingstone in type and very good in flavor, but is distinguished therefrom by producing fruit that is larger in size, that has more red bleeding in the flesh, that has a bitter instead of sweet kernel, and that matures about five days later.

SUMMARY OF VARIETY

In summary, the present nectarine variety is characterized by a large size, vigorous, hardy, self-fertile, productive and regular bearing tree. The variety blooms during the mid season and requires about 525 chilling hours. The fruit matures under the ecological conditions described in mid June, with first picking on Jun. 10, 2016. The fruit is large in size, globose to slightly oblong in shape, clingstone in type, firm in texture, yellow with red bleeding in flesh color, full red in skin color, and acidic in flavor.

DRAWING

The accompanying photograph consists of four whole fruits positioned to display the characteristics of the skin color and form, one divided fruit to reveal the flesh and stone, characteristic leaves, and two insets to reveal flower buds and a blossom as they appeared on the tree during the blooming season.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 14, 2016 on the original tree during the eighth growing season. The blossom and flower descriptions were made the previous blooming season. All major color code designations are by reference to the Inter-Society Color Council, National Bureau of Standards. Common color names are also used occasionally.

It is to be noted that the 2016 fruit season in California was very warm during the spring and the ripening times of almost all varieties were about two weeks earlier than most other years.

PARENTAGE

Seed parent: '5P452' (unpatented) nectarine.

Pollen parent: 'Kay Diamond VII' (U.S. Plant Pat. No. 18,715) nectarine.

TREE

Size: Large, reaching and maintaining a height of 14' [4.27 m.] and a spread of 14' [4.27 m.] after eight growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and require regular irrigation.

Production: Productive, thinning necessary.

Fertility: Self-fertile.

Bearing: Regular bearer with no alternate bearing yet observed.

Approximate chilling requirement: 525 hours.

Trunk:

- *Size*.—Medium, reaching a maximum diameter of 4" [102 mm.] after the eighth growing season.
- *Texture*.—Medium, shaggy.
- *Bark color*.—A Light grayish yellowish brown [79. l.gy.yBr] and Grayish yellowish brown [80. gy.yBr] variegation with Brownish gray [64. brGy] crevices present.
- *Lenticels*.—Approximate Number Per Square Inch: 6. Color: Moderate yellowish brown [77. m.yBr]. Average Size: ⅛" [3.2 mm.] in length. The width is typically one fourth as much as the length. Shape: Eye-shaped.

Branches:

- *Size*.—Medium, diameter of main scaffold is 2½" [63.5 mm.] measured 12" above crotch, diameter of limb is 1¼" [31.8 mm.] measured 12" above first fork.
- *Texture*.—Smooth to medium on first and second year wood, increasing in roughness with age.
- *Color*.—1st Year Wood Topside: Grayish red [19. gy.R]. 1st Year Wood Underside: Brilliant yellow green [116. brill.YG]. Older Wood: A Light brown [57. l.Br] and Moderate brown [58. m.Br] variegation with Grayish blown [61. Gy.Br] crevices present.
- *Lenticels*.—Number Per Square Inch: About 60 on second year wood. Color: Light yellowish brown [76. l.yBr]. Average size: Medium, 1/16" [1.6 mm.] in length on second year wood. The width is typically one fourth as much as the length. Shape: Eye-shaped.

Leaves:

- *Size*.—Very large. Average Length: 7" [178 mm.]. Average Width: 2 1/16" [52.4 mm.].
- *Arrangement*.—Alternate.
- *Thickness*.—Medium.
- *Form*.—Elliptical.
- *Apex*.—Acuminate.
- *Base*.—Acute.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Vein color*.—Light yellow green [119. l.YG].
- *Petiole*.—Average Length: ½" [12.7 mm.]. Average Thickness: ⅛" [3.2 mm.]. Color: Light yellow green [119. l.YG] becoming Strong yellow green [117. s.YG] with age.
- *Stipules*.—Number: Usually 2 per leaf, up to 6 per growing tip. Average Length: ⅜" [9.5 mm.]. Color: Brilliant yellow green [116. brill.YG] becoming Moderate reddish brown [43. m.rBr] with maturity.
- *Glands*.—Number: 2 to 4 per leaf. Position: Mostly alternate, near the intersection of the petiole and base of blade. Form: Globose. Size: Medium, about 1/32" [0.8 mm.] in diameter. Color: Light yellow green [119. l.YG] becoming Moderate reddish brown [43. m.rBr] with age.
- *Leaf buds*.—Pointed, medium in size.

Flower buds:

- *Hardiness*.—Hardy, with respect to central California blooming season.
- *Diameter*.—Typically 5/16" [7.9 mm.] 1 week before bloom.
- *Length*.—Typically ⅝" [15.9 mm.] 1 week before bloom.
- *Form*.—Free, not touching.
- *Surface*.—Pubescent.
- *Tip color*.—Light pink [4. l.Pk].

Flowers: Perfect, complete, perigynous, usually a single pistil, about thirty stamens, five sepal and petal locations alternately positioned.

*Type*.—Showy, large.

*Average flower diameter*.—2⅛" [54.0 mm.].

*Average flower depth*.—½" [12.7 mm.] when fully open.

*Number of petals*.—Usually five, extra petal fragments commonly occur, double blossoms rarely observed.

*Petal arrangement*.—Overlapping.

*Petal shape*.—Circular to oval.

*Petal margin*.—Entire, somewhat wavy, occasional notches.

*Average petal diameter*.—13/16" [20.6 mm.].

*Average petal length*.—⅞" [22.2 mm.].

*Petal apex*.—Rounded.

*Petal base*.—Rounded to somewhat truncate.

*Petal color*.—Pale pink [7. p.Pk] toward the apex, Light pink [4. l.Pk] toward the base on both sides.

*Anther color*.—Strong red [12. s.R] over a Light yellow [86. l.Y] center at bloom onset.

*Pollen*.—Anthers produce an abundance of Brilliant yellow [83. brill.Y] pollen.

*Stigma color*.—Light greenish yellow [101. l.gY].

*Stigma position*.—Typically located about even with the nearby anthers.

*Stamen position*.—Typically located about 1/32" [0.8 mm] below the petals.

*Average pistil length*.—¾" [19.1 mm.].

*Average stamen length*.—⅝" [15.9 mm.].

*Ovary*.—Smooth.

*Sepal color*.—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.

*Sepal length*.—¼" [6.4 mm.].

*Sepal width*.—3/16" [4.8 mm.].

*Sepal apex*.—Rounded to elliptical to match the sepal length and width.

*Fragrance*.—Moderate.

*Blooming period*.—Medium, at the same time as 'Spring Bright' (U.S. Plant Pat. No. 7,507) nectarine.

*Onset of bloom*.—One percent on Feb. 15, 2016.

*Date of full bloom*.—Feb. 24, 2016.

*Duration of bloom*.—One to two weeks, dependent on ambient temperature.

*Bloom density*.—Medium to heavy.

*Number per cluster*.—1 to 3 with single flowers most common.

FRUIT

Maturity when described: Firm ripe, Jun. 14, 2016.

Date of first picking: Jun. 10, 2016.

Date of last picking: Jun. 20, 2016.

Size: Large, mostly uniform.

*Average diameter axially*.—3 1/16" [77.8 mm.].

*Average diameter across suture plane*.—3 [76.2 mm.].

*Average diameter across cheek plane*.—2⅞" [73.0 mm.].

*Typical weight*.—8.9 ounces [252 grams].

Form: Globose to slightly oblong, slightly asymmetrical.

*Longitudinal section form*.—Round, slightly oblong.

*Axial view*.—Round.

Suture: A shallow trough extending from the base to just beyond the pistil point.

*Near the base*.—A shallow groove.

*Along the side*.—A shallow trough.

*Near the apex*.—A shallow groove.

Ventral surface: Rounded, lipped on both sides.

Lips: Slightly unequal.

Cavity: Flaring, suture showing on one side, Very orange yellow [66. v.OY] stem markings typical.

*Depth*.—½" [12.7 mm.].

*Breadth*.—1⅛" [28.6 mm.].

Base: Truncate, very slightly cordate if viewed parallel to the suture.

Apex: Rounded, cordate if viewed parallel to the suture.

Pistil point: Apical, negligible in length, usually depressed within the suture.

Stem: Medium.

*Average length*.—7/16" [11.1 mm.].

*Average width*.—⅛" [3.2 mm.].

Skin:

*Thickness*.—Medium.

*Surface*.—Smooth.

*Tenacity*.—Tenacious to flesh.

*Astringency*.—Astringent.

*Tendency to crack*.—None observed.

*Color*.—Very deep red [14. v.deep R] over a Moderate red [15. m.R] background with moderate Light yellow [86. l.Y] freckling toward the apex.

Flesh:

*Color*.—Brilliant orange yellow [67. brill.OY] with Dark red [16. d.R] bleeding and flecking throughout.

*Surface of pit cavity*.—Covered with Strong orange yellow [68. s.OY] broken fibers when twisted from the stone.

*Amygdalin*.—Moderate.

*Juice*.—Moderate, rich.

*Texture*.—Firm, crisp.

*Fibers*.—Abundant, fine, tender.

*Ripens*.—Fairly evenly.

*Flavor*.—Acidic, ample sugar, typically 14 brix.

*Aroma*.—Very slight.

*Eating quality*.—Very good.

STONE

Type: Clingstone.

Form: Oval.

Hilum: Narrow, oval.

Base: Slightly rounded.

Apex: Acuminate.

Sides: Slightly unequal.

Tip: Sharp, approximately 1/16" [1.6 mm.] in length.

Surface: Irregularly furrowed toward the apex, pitted toward the base.

Ridges: Jagged.

External color: Moderate orange yellow [71. m.OY].

Pit wall color when cracked: Light orange yellow [70. l.OY].

Cavity surface color: Light yellowish brown [76. l.yBr] with Dark orange yellow [72. d.OY] areas toward the apex.

Average pit wall thickness: ¼" [6.4 mm.].

Average length: 1⅝" [41.3 mm.].

Average width: 1⅛" [28.6 mm.].

Average breadth: ⅞" [22.2 mm.].

Tendency to split: None observed.

Kernel:

*Form*.—Oval.

*Skin color*.—Light yellow [86. l.Y] when first removed.

*Pellicle color*.—Deep yellowish brown [75. deep yBr].

*Vein color*.—Light brown [57. l.Br].

*Taste*.—Bitter.

*Viable*.—Yes.

*Average length*.—13/16" [20.6 mm.].

*Average width*.—7/16" [11.1 mm.].

*Amygdalin*.—Abundant.

USE

Market: Fresh market and long distance shipping.

Keeping quality: Good, fruit quality observed to remain in good condition after 21 days in standard cold room at 36° Fahrenheit [2° Celsius].

Shipping quality: Good.

Resistance to insects: No unusual susceptibilities noted.

Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to 'Spring Bright' (U.S. Plant Pat. No. 7,507) nectarine by being self-fertile, by blooming in the mid season, by having globose leaf glands, and by producing nectarines that are firm in texture, mostly red in skin color, yellow in flesh color, nearly globose in shape, clingstone in type and very good in flavor, but is distinguished therefrom by producing fruit that is larger in size, that has more red bleeding in the flesh, that has a bitter instead of sweet kernel, and that matures about five days later.

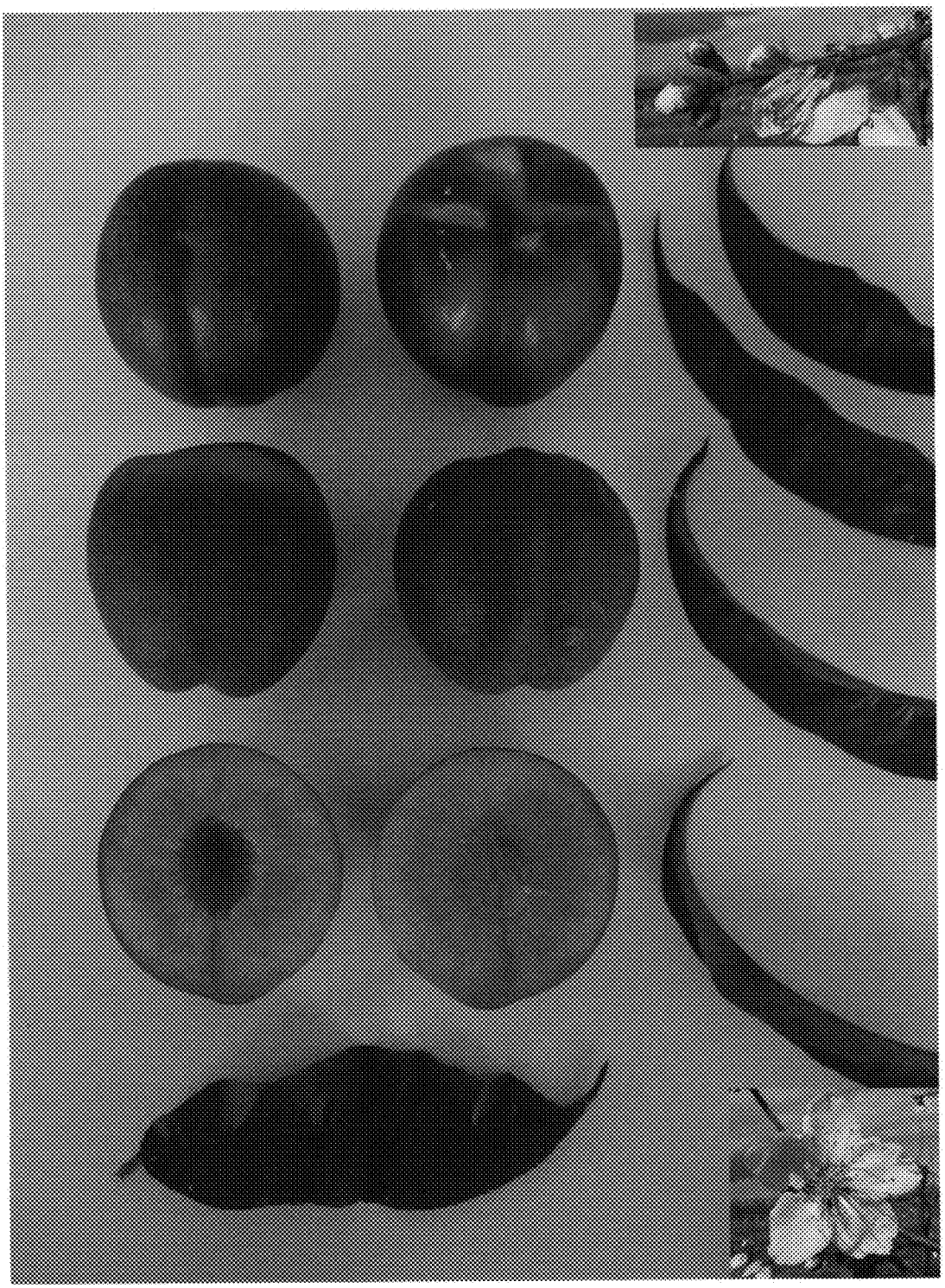

* * * * *